United States Patent [19]
Rensimer et al.

[11] Patent Number: 5,845,253
[45] Date of Patent: *Dec. 1, 1998

[54] SYSTEM AND METHOD FOR RECORDING PATIENT-HISTORY DATA ABOUT ON-GOING PHYSICIAN CARE PROCEDURES

[75] Inventors: Edward R. Rensimer, Houston, Tex.; Jacqueline P. Tomsovic, Tulsa, Okla.; Pamela A. Wright, Houston, Tex.

[73] Assignee: Rensimer Enterprises, Ltd., Houston, Tex.

[ * ] Notice: The terminal 2 months of this patent has been disclaimed.

[21] Appl. No.: 296,311

[22] Filed: Aug. 24, 1994

[51] Int. Cl.$^6$ ................................................. G06F 159/00
[52] U.S. Cl. ....................................... 705/2; 705/3
[58] Field of Search .......................... 364/401 R, 401 M, 364/413.01, 413.02; 705/2, 3; 128/920, 923

[56] References Cited

U.S. PATENT DOCUMENTS

| | | |
|---|---|---|
| 4,591,974 | 5/1986 | Dornbush et al. . |
| 4,667,292 | 5/1987 | Mohlenbrock et al. . |
| 4,839,806 | 6/1989 | Goldfischer . |
| 5,018,067 | 5/1991 | Mohlenbrock et al. . |
| 5,325,293 | 6/1994 | Dorne . |
| 5,483,443 | 1/1996 | Milstein et al. . |
| 5,519,607 | 5/1996 | Tawil . |

OTHER PUBLICATIONS

Physician's Current Procedural Terminology, Fourth Edition, CPT '94, American Medical Association, pp. i–86 and 683, 1994.
Fishman, Scott M., "Study Tracks Effectiveness of HP Palmtop in Hospital," The HP Palmtop Paper, May–Jun. 1994, pp. 34–35.
Hall, Rich, "A Less Expensive Solution to Healthcare?" The HP Palmtop Paper, May–Jun. 1994, pp. 27–29.
Meissner, Frank, "User Profile: HP Palmtop: A 24–Hour Medical Assistant," The HP Palmtop Paper, May–Jun. 1994, pp. 12–16.
Peak, Dallas E., "User Profile: Doctor on the Fly Uses the HP Palmtop to Help Save Lives," The HP Palmtop Paper, May–Jun. 1994, pp. 18–21.
Special Report: Computer & Communications (Collection of related articles), ACP Observer, vol. 14, No. 7, Jun. 1994, pp. 19–29.
Advertisement: PEPID, a Palmtop Emergency Physician Information Database product.
Advertisement Listing: Medical and Health–Related Hardware and Software, The HP Palmtop Paper, May/Jun., 1994, pp. 36–39.

*Primary Examiner*—Robert A. Weinhardt
*Attorney, Agent, or Firm*—Arnold, White & Durkee

[57] ABSTRACT

A system and method for processing patient data permits physicians and other medical staff personnel to record, accurately and precisely, historical patient care information. An objective measure of a physician's rendered level of care, as described by a clinical status code, is automatically generated. Data elements used in the determination of the generated clinical status code include a level of history of the patient, a level of examination of the patient, a decision-making process of the physician treating the patient, and a "time influence factor." The quantity and quality of care information for a particular patient is enhanced allowing future care decisions for that patient to be based on a more complete medical history. Enhanced care information can be used in outcome studies to track the efficacy of specific treatment protocols. Archiving of patient information is done in a manner which allows reconstruction of the qualitative aspects of provided medical services. The medical care data can be recorded, saved, and transferred from a portable system to a larger stationary information or database system. Considerable physician and staff time are saved and precision and accuracy are significantly enhanced, by generating these clinical status codes automatically (at the point of service by the care-provider without any intermediary steps) from information recorded simultaneously with the provision of services.

18 Claims, 7 Drawing Sheets

Microfiche Appendix Included
(7 Microfiche, 571 Pages)

```
┌──────── Patient Detail SMITH, HENRY ─────────┐
│Last Name: SMITH                              │
│First Name: HENRY                             │
│Date Involved: 01/31/1994                     │
│Hospital: HIL                                 │
│Stat    ┌───── Patient Diagnosis ─────┐       │
│[N]e    │ ☐                           │       │
│Diag    └───── F2=Save Esc=Abort ─────┘       │
│Referring Phys:                               │
│Admitted: 1/25/1994    DOB: 3/14/1967         │
│Planned Release Date:   / /                   │
│Actual Release Date:    / /                   │
│Regular Phys: BEASLEY, BRENT                  │
│Patient Phone: (   )   -                      │
│Problem Pt.: ADDITION PRSNAL                  │
└F1=Help F2=Save F3=Lookup ESC=Exit────────────┘
```

FIG. 3A

```
┌──────── Patient Detail SMITH, HENRY ─────────┐
│La┌───────────── Diagnoses ──────────┐        │
│Fi│ AIDS                             │        │
│Da│ ANEMIA                           │        │
│Ho│ ASTHMA                           │        │
│St│ COLD BLOOD                       │        │
│[N│ ENTERIC F.                       │        │
│Di│ CRYPTOSPOR.                      │        │
│Re│ DYSENTERY                        │        │
│Ad│ TB-TUBERCULOSIS                  │        │
│Pl│ MAI-C                            │        │
│Ac│ SEPSIS                           │        │
│Re│ MRSA INFECTION                   │        │
│  └──────────── adding ──────────────┘        │
│                                              │
└──────────────────────────────────────────────┘
```

FIG. 3B

```
┌──────── Charge Entry #1- KIDD, TOM ────────┐
│       Type: 1 -Visit                       │
│────────────────────────────────────────────│
│  Serv. Type:                               │
│     Hist┌──────── Service type ────────┐   │
│  Examinat│ 1 -Office and Outpatient    │   │
│  M. Decis│ 2 -Hospital Inpatient       │   │
│          │ 3 -Consultation Outpatie    │   │
│   Proced │ 4 -Consultation Inpatien    │   │
│   Diagno │ 5 -Consultation Confirm     │   │
│          │ 6 -Emergency                │   │
│   Time < │ 7 -Critical Care            │   │
│     CPT Code:            Modifier:         │
└── F2=Save  F3=Lookup  F5=Another  ESC=Exit ┘
```

FIG. 4

```
┌──────── Charge Entry #1- KIDD, TOM ────────┐
│       Type: 1 -Visit                       │
│────────────────────────────────────────────│
│  Serv. Type: 1 -Office and Outpatient      │
│     History:    ┌──── History ────┐        │
│  Examinat       │ 1 -Problem Focused │     │
│  M. Decis       │ 2 -Expanded        │     │
│                 │ 3 -Detailed        │     │
│   Procedu       │ 4 -Comprehensive   │     │
│   Diagnos       └────────────────────┘     │
│────────────────────────────────────────────│
│  Time < optional >:                        │
│     CPT Code:            Modifier:         │
└── F2=Save  F3=Lookup  F5=Another  ESC=Exit ┘
```

FIG. 5

Office (outpatient visits) Services
   Ques? Any symptoms?
      no = Ques? Give Physical?
         no = Ques? Provided Counseling?
           no = 99499
           yes = Prompt = go to counseling or risk reduction factor
     yes = using Preventative Medicine yes = use table below

NEW (3/3) ">50% CONTACT COUNSELING/COORDINATION"

| HISTORY | EXAM | MEDICAL DECIS. | TIME | CODE |
|---|---|---|---|---|
| PROBLEM FOCUSED | PROBLEM FOCUSED | STRAIGHT FORWARD | <=19 | 99201 |
| EXPANDED | EXPANDED | STRAIGHT FORWARD | >=20<=29 | 99202 |
| DETAILED | DETAILED | LOW COMPLEXITY | >=30<=44 | 99203 |
| COMPREHENSIVE | COMPREHENSIVE | MODERATE | >=45<=59 | 99204 |
| COMPREHENSIVE | COMPREHENSIVE | HIGH | >=60 | 99205 |

ESTAB (2/3) ">50% CONTACT COUNSELING/COORDINATION"

| HISTORY | EXAM | MEDICAL DECIS. | TIME | CODE |
|---|---|---|---|---|
|  |  |  |  |  |
| FOCUSED | FOCUSED | STRAIGHT FORWARD | >=11<=10 <=14 | 99212 |
| EXPANDED | EXPANDED | LOW COMPLEXITY | >=15<=24 | 99213 |
| DETAILED | DETAILED | MODERATE | >=25<=39 | 99214 |
| COMPREHENSIVE | COMPREHENSIVE | HIGH | >=40 | 99215 |

FIG. 6

SYSTEM AND METHOD FOR RECORDING PATIENT-HISTORY DATA ABOUT ON-GOING PHYSICIAN CARE PROCEDURES

REFERENCE

Certain aspects of the instant invention are similar to those disclosed in U.S. patent application Ser. No. 08/259,338 filed May 13, 1994, now abandoned entitled "Portable Patient Data Processing System and Method" by Edward R. Rensimer. Application Ser. No. 08/259,338 is a continuation of U.S. patent application Ser. No. 07/877,868, filed May 4, 1992 and commonly owned with the instant application. Both applications are incorporated here, in their entirety, by reference.

Included are microfiche appendices A, B and C of seven microfiche of 571 total frames.

Additionally, certain terminology and definitions described in the 1994 edition of the Physicians' Current Procedural Terminology manual (referred to as CPT or CPT94) are incorporated herein by reference. The CPT manual provides a standard classification of medical procedures and is well known to those of ordinary skill in the field.

2. BACKGROUND OF THE INVENTION

The invention relates to a hand-held physician's computer and database system configured to collect, store, and report historical patient-care information at the site of patient service. The system and method permits a physician, or other care-provider, to record not only patient status information but, importantly, other patient-treatment information as well Many prior patient data systems focused more on data about current patient status than on historical data about the care given to the patient. Such data conveyed comparatively little or no information about the physician and other medical-staff resources that were previously utilized in caring for the patient. One of the most common methods of recording patient care information is the so-called superbill. The superbill is a multipart paper form that is preprinted with numerous broad categories of standard services. The physician checks off one or more of the categories of care, and might make handwritten notes about the specific diagnosis and/or services provided (e.g., otitis media or amoxicillin). The superbill has several drawbacks, including a comparative lack of precision or "granularity" because of the limited space on the preprinted paper form.

3. SUMMARY OF THE INVENTION

A system and method for building more complete patient history data permits physicians and other medical staff personnel to record, accurately and precisely, the treatment or care given in a particular patient encounter. One benefit of the invention is the generation of an objective measure of a physician's rendered level of care, as described by a clinical status code, in a novel modification of a standard classification system. Data elements used in the determination of the clinical status code include a level of history of the patient, a level of examination of the patient, a decision-making process of the physician treating the patient, and a "time influence factor."

Other attendant benefits of the invention include: (1) enhancement of the quantity and quality of care information for a particular patient, allowing future care decisions for that patient to be based on a more complete medical history; (2) enhanced care information can be used in outcome studies to track the efficacy of specific treatment protocols; (3) historical data about physician workload can be easily gathered which, in turn, can contribute to a better understanding and allocation of the professional resources actually used in a given practice during a particular period of time; (4) generated clinical status codes can be used in requesting payment for medical services from insurance companies or other payors; (5) archiving of patient information in a manner which allows reconstruction of the qualitative aspects of provided medical services; (6) real-time sharing and communication of clinical data between physicians; (7) standardization of nomenclature used by groups of physicians in caring for patients; (8) automatic and clean data capture and storage of medical record data that would otherwise be done manually, and (9) the ability to record, transfer, and save medical care data from a portable system to a larger stationary informnation or database system. Considerable physician and staff time are saved, and the precision and accuracy of patient treatment history are significantly enhanced, by recording these activities contemporaneously with the service rendered.

4. BRIEF DESCRIPTION OF DRAWINGS

FIGS. 3A and 3B are two screen views of an exemplary "patient diagnosis" prompt window in accordance with the invention.

FIG. 4 is a screen view of an exemplary "patient service type" prompt window in accordance with the invention.

FIG. 5 is a screen view of an exemplary "key element level" select prompt window in accordance with the invention.

FIG. 6 is an exemplary logic table describing a means of determining a clinical status code for a service type of "Office (outpatient visit) Services". See also microfiche Appendix A.

5. DETAILED DESCRIPTION OF A SPECIFIC EMBODIMENT

One illustrative embodiment of the invention is described below as it might be implemented using a hand-held general purpose computer. In the interest of clarity, not all features of an actual implementation are described in this specification. It will of course be appreciated that in the development of any such actual implementation (as in any development project), numerous implementation-specific decisions must be made to achieve the developers' specific goals and subgoals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

Microfiche Appendix A contains a listing of clinical status code selection logic tables in accordance with the invention. Microfiche Appendix B contains source code listings, in the 'C' programming language, that embody one implementation of the inventive method. Microfiche Appendix C contains documentation for certain aspects of one embodiment of the invention (see source code listings, Appendix B).

Microfiche appendixes A, B, and C contain a total of 7 sheets and 571 frames.

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright and similar rights whatsoever.

5.1 Apparatus

Figure 1:
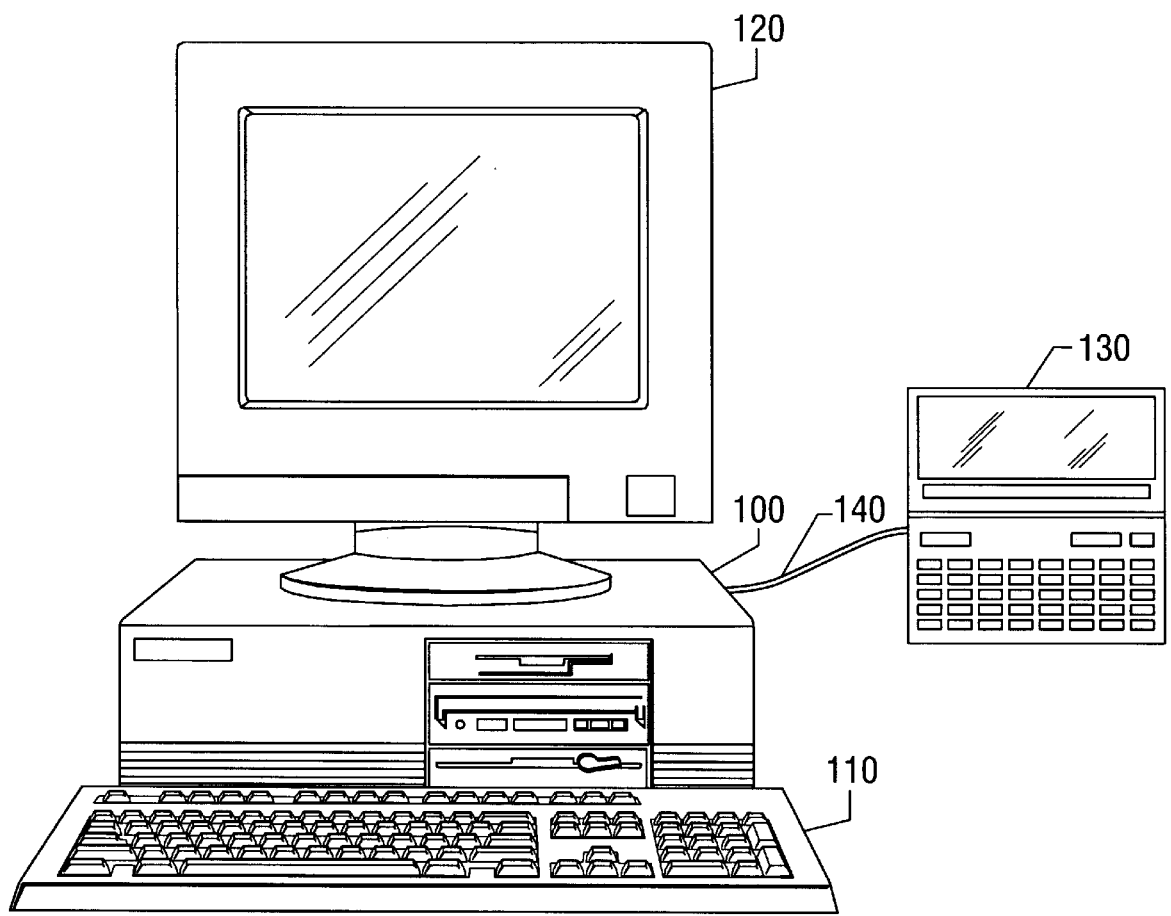
FIG. 1 is a block diagram of a portable patient data processing system in accordance with the invention.

FIG. 1 shows two personal computers, depicting an overall representation of a system in accordance with the present invention. The first is a relatively stationery desktop personal computer comprising a CPU chassis 100, to which is coupled a keyboard 110 and a CRT display 120. The desktop personal computer is, in the preferred embodiment, an IBM compatible personal computer. FIG. 1 further shows personal computer 130 of the hand-held type, which is, in the preferred embodiment, of a bivalve type (e.g., Hewlett-Packard 100 and 200 LX series of computers, although the present invention is not limited to these specific computing hardware types). That is, it opens in a clamshell manner to reveal therein a screen and keyboard, not separately referenced. The first and second personal computers are disconnectedly coupled by a link 140 comprising, for example, a plurality of separate wires in a bundle or alternatively an optical or radio link of the kind well-known in the art. (The HP 100LX and HP 200LX hand-held computers have infrared optical links built-in.). It is irrelevant for purposes of the present invention that the link 140 be a parallel or serial link; either one is contemplated.

In the preferred embodiment, the hand-held personal computer 130 is designed to be detached from the desktop personal computer and taken with the physician, or other medical care-taker, on his clinical rounds to enter and extract information. When the physician returns from his clinical activities, the hand-held personal computer 130 may be rejoined to the desktop personal computer by means of the link 140 to thereby transfer information there between.

5.2 Method

Figure 2:
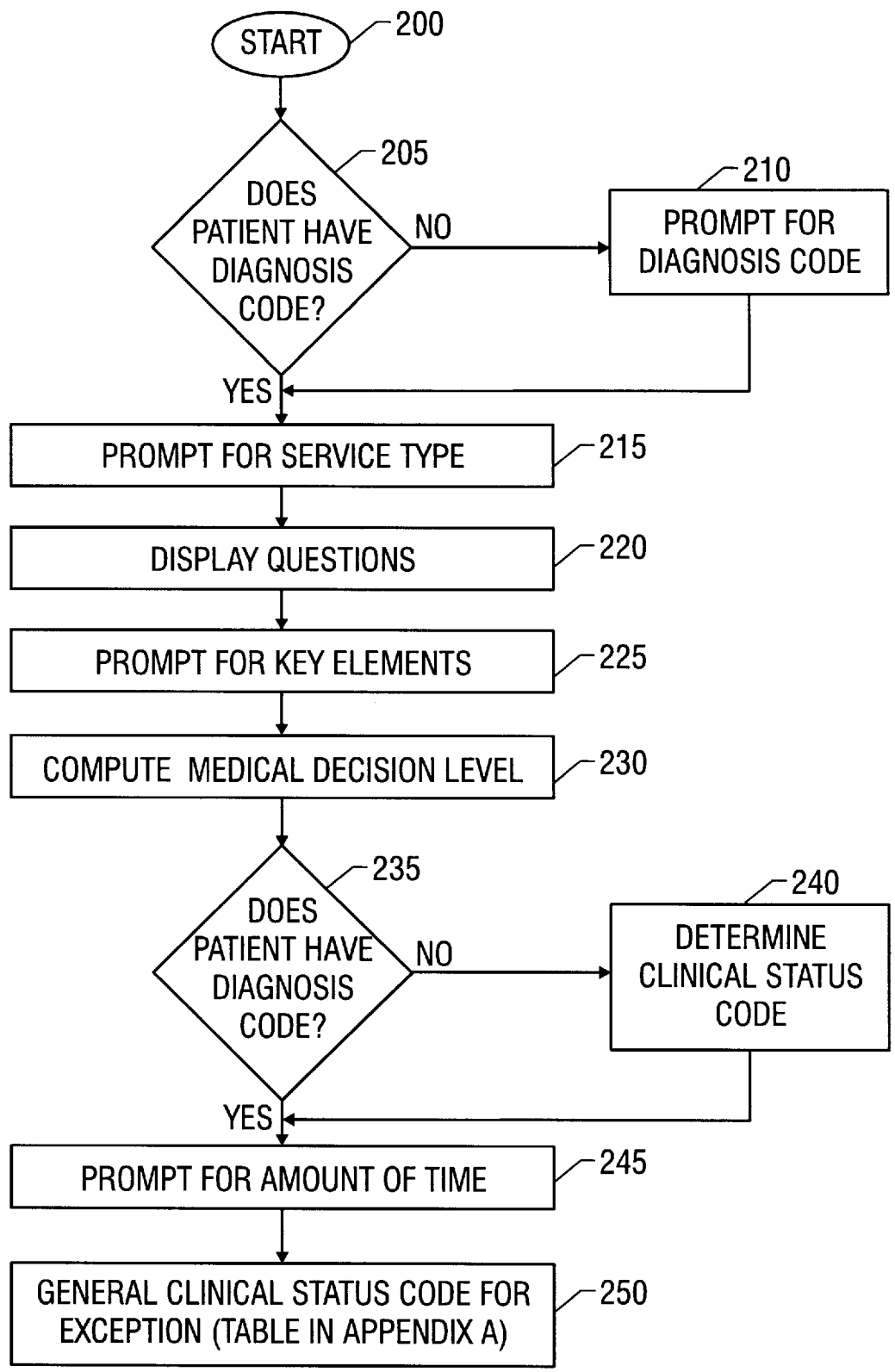
FIG. 2 is a high level flow diagram of a method in accordance with the invention.

FIG. 2 shows a high-level view of a method (executed by a device such as hand-held computer 130 and operated by medical professional staff) of generating a signal quantifying a physician intervention status of a patient. The signal is referred to for convenience as a "clinical status code." It will be apparent that the device can be intuitively operated by multiple medical staff members in sequence, e.g., by a nurse, a physician, an office administrator, a receptionist, and the like, to the extent consistent with proper medical practice. Individual steps, outlined in FIG. 2, are discussed in more detail below.

5.3 Clinical Status Code Components of a Patient

The clinical status code is a function of a number of patient-related items. Three such items are referred to as "key elements" of the clinical status code, namely (1) a level of medical history of the patient, (2) a level of physical examination of the patient, and (3) a medical decision-making process of the physician treating the patient. A fourth important patient-related factor is a "time influence factor."

The level of history and level of examination are standard indicators, defined in the CPT manual, of the intensity of service rendered by medical personnel in obtaining patient history and in examining the patient. Four standard levels are associated in each of the level of history and level of examination. These levels are (1) problem-focused; (2) expanded problem-focused; (3) detailed; and (4) comprehensive.

The decision-making process of a physician treating the patient refers to CPT-standard indicators of three different decision components: (1) risk of complications and/or morbidity or mortality, referred to simply as "risk;" (2) the amount and/or complexity of data to be reviewed, referred to simply as "complexity;" and (3) the number of diagnoses or management options considered by the physician, referred to simply as "diagnoses." Each of the three decision components has four possible levels:

| Decision Component | Level |
|---|---|
| 1. Risk | Minimal |
| | Low |
| | Moderate |
| | High |
| 2. Complexity | Minimal or None |
| | Limited |
| | Moderate |
| | Extensive |
| 3. Diagnoses | Minimal |
| | Limited |
| | Multiple |
| | Extensive |

The time influence factor refers to an adjustment to the CPT-standard amount of time associated with a particular CPT clinical status code. The adjustment takes into account the physician's actual work time associated with a patient encounter, as a function of an amount of unit floor time (or face-to-face time) spent by the physician in connection with the patient encounter, or of an amount of time spent by the physician in counseling or coordination of care for the patient.

Consider a hypothetical example of a time influence factor: A clinical status code of "1-1-1" represents a new-patient encounter, i.e., an encounter at the lowest level of history, examination, and decision making process for a new patient, is associated with a CPT-standard amount of time of 10 minutes. If the encounter is prolonged to 20 minutes because of, say, an extended face-to-face discussion between the patient and physician (or with the patient's spouse, parent, or other responsible party, e.g., a person holding a medical power of attorney), a time influence factor is entered to reflect the extra 10 minutes spent by the physician in the patient encounter and may modify the clinical status code generated in accordance with the invention.

5.4 Steps for Determining a Patient's Clinical Status Code

The method steps shown in FIG. 2 are as follows:

200 Start of a method in accordance with the invention.

205 A data store (not shown) is consulted to determine whether a diagnosis already exists for the patient in question.

210 If a diagnosis does not exist, the user is prompted to select a diagnosis; a diagnosis code representing the selected diagnosis for the patient is stored in the data store. FIG. 3 shows views of two diagnosis prompt windows. FIG. 3A is a generic Diagnosis prompt window while FIG. 3B shows a partial (exemplary) list of possible diagnoses. If the staff member determines that the available diagnoses presented for selection not adequately describe the diagnosis for the patient, the staff member may enter an additional diagnosis by selecting a conventional "Add New Diagnosis" function. The staff member is then given the option of placing the newly added diagnosis into a master diagnosis table. Staff members can then select the newly added diagnosis during the normal course of clinical evaluations.

215 The staff member is prompted to select a service type, referred to as a selected service type, as shown in FIG. 4. The CPT-standard service types are: (a) outpatient services, (b) hospital observation services, (c) hospital inpatient services, (d) hospital discharge services, (e) outpatient consultations, (f) inpatient consultations, (g) inpatient follow-up consultations, (h) confirmatory consultations, (i) emergency services, (j) critical care visits, (k) neonatal intensive care, (1) nursing facility services, (m) domiciliary, rest home, or custodial care, (n) home services, (o) prolonged services, (p) case management team services, (q) case management phone services, (r) care plan oversight services, (s) preventive medicine services, (t) preventive medicine individual counseling, (u) preventive medicine group counseling, and (v) newborn care.

Figure 7A:
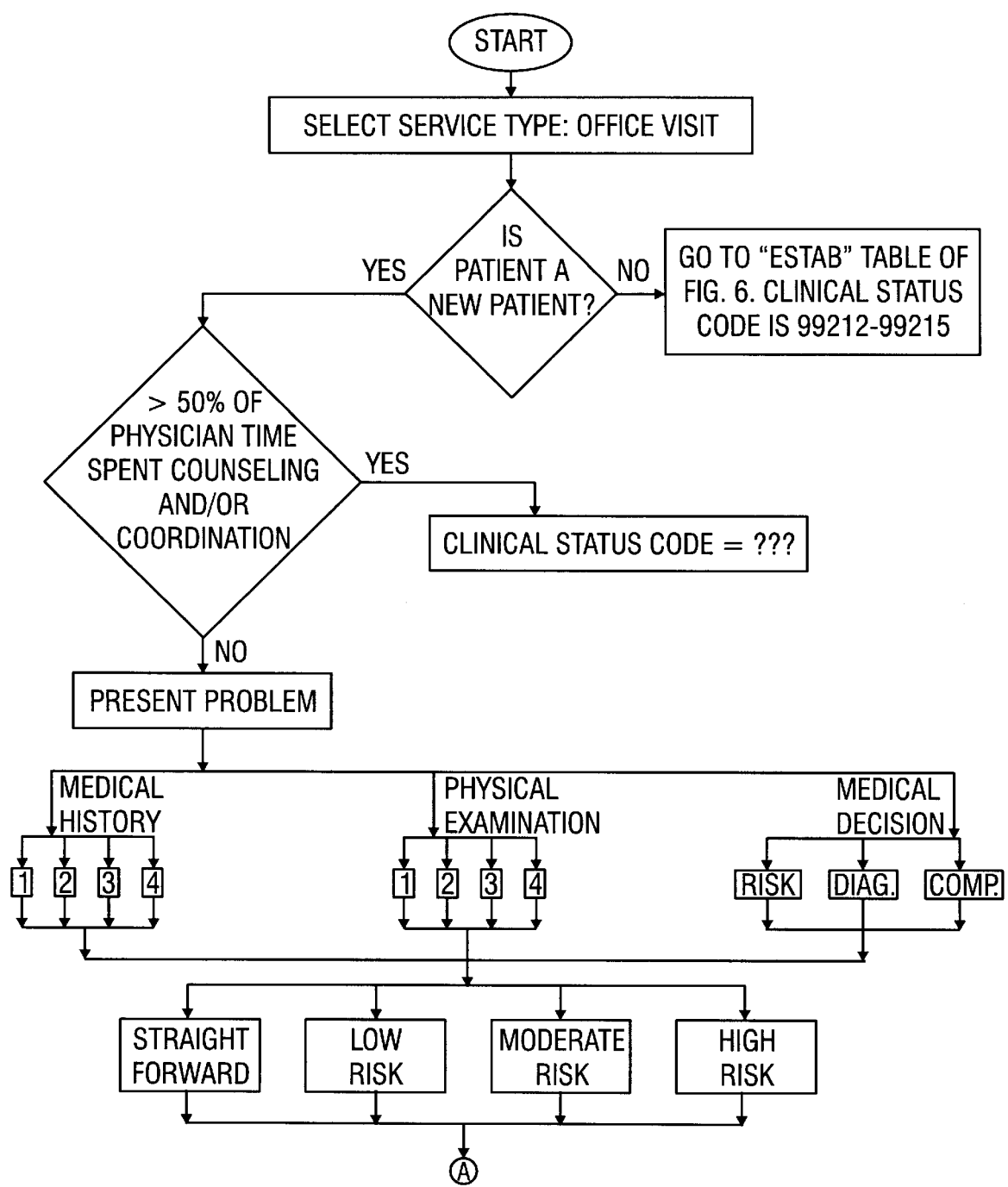
FIG. 7 is a flow diagram for FIG. 6.
Figure 7B:
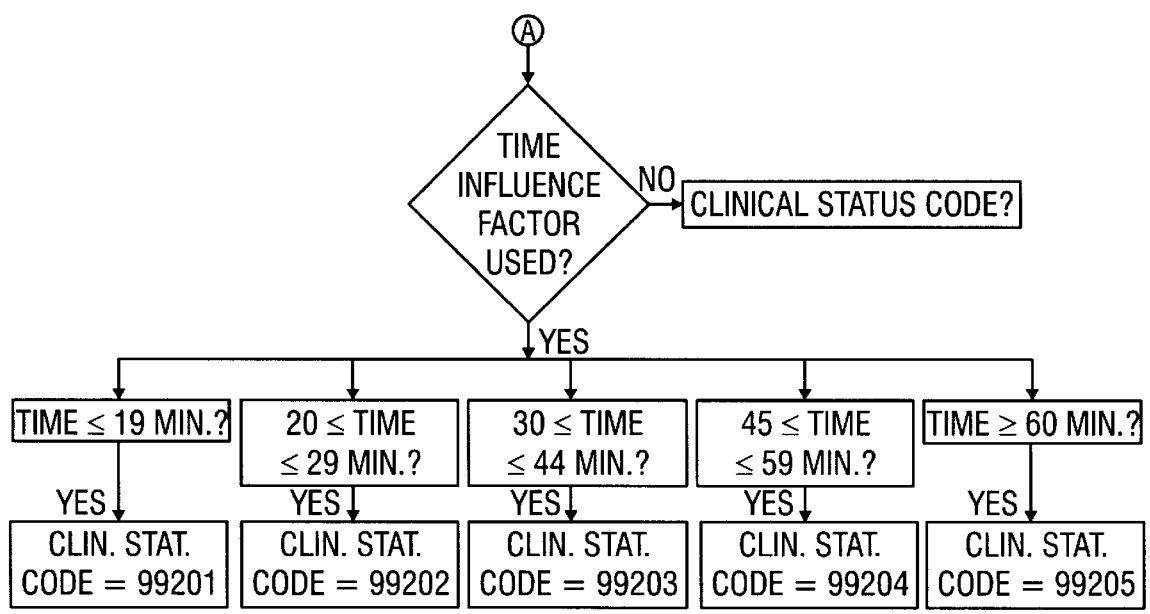

220 A series of questions are displayed to the staff member. The questions are designed and arranged for enhanced human-factors ("ergonomic") effectiveness to obtain quickly certain information needed for determining the clinical status code. The specific questions asked are determined in part by the selected service type. The answer to any given question may influence which questions are subsequently asked. A specific set of questions, primarily of the yes-no variety, are reproduced in the source-code listings of microfiche Appendix B of this application; a specific example is discussed in connection with FIGS. 6 and 7 below.

225 The staff member is prompted to select, for each respective key element (see discussion above), a level for the key element. An exemplary key element level screen prompt is shown in FIG. 5.

230 From the selected levels for the decision-making process, a specific level for the type of medical decision making (straightforward, low complexity, moderate complexity, high complexity) is computed in accordance with the table on page 13 of CPT94. It will be understood, of course, that the level of medical decision-making can be computed later as part of the ultimate determination of the clinical status code.

235 A test is made to determine whether the selected service type falls within an exception category. Exception categories include (a) hospital discharge services, (b) observation discharge services, (c) critical care, (d) care plan oversight services, (e) case management team services, (f) prolonged services, (g) neonatal intensive care, (h) case management phone services, (i) preventive medicine services, (j) emergency advanced life support services, and (k) newborn care.

240 If the selected service type does not fall within an exception category, then the clinical status code is determined as a function of one or more of (1) the selected service type; (2) the selected levels, including the computed level of medical decision making; and (3) if the physician entered an amount of service time, the amount of service time. Determination of a clinical status code is made in accordance with the logic tables shown in microfiche Appendix A.

245 If the selected service type is associated with a time influence factor, then the physician is prompted to enter an amount of service time.

250 Determination of an "exception" clinical status code, as set forth above, is made in accordance with the logic tables given in microfiche Appendix A.

Table 1 shows a set of service-type guidelines for using the key elements and the physician's time influence factor in selecting a clinical status code. It will be appreciated by those of ordinary skill having the benefit of this disclosure that Table 1 provides a novel and concise alternative encoding of the CPT rules set forth on pages 13–14 of CPT94. Table 1 is one of the tables comprising microfiche Appendix A.

TABLE 1

Service type Guidelines
Definitions: N = New patient, E = Established patient
upper area: History, Exam, Medical Decision key elements
50% question: amount of time spent in face-to-face contact with patient

| Must meet or exceed all of the key components of history, exam, medical decision-making (3/3) | Time | Must meet two of the three key components of history, exam, and medical decision-making (2/3) |
|---|---|---|
| Office: (outpatient) (N) | Factor | Office: (outpatient) (E) |
| Hospital observation services (N/E) | | |
| Initial hospital care (N/E) | Factor | Subsequent Hospital Care |
| Office Consult (outpatient) (N/E) | Factor | |
| Initial Inpatient Consult (N/E) | Factor | Follow-up Inpatient Consultation (E) |
| Confirmatory Consult (N/E) | | No 50% question |
| Emergency Department | | |
| Critical care | Factor | No 50% question (30 minute increments) |
| Neonatal Intensive Care | | No 50% question |
| Comprehensive Nursing Facility (N/E) | Factor | Subsequent Nursing facility care (N/E) |
| Domiciliary Care (rest home): (N) | | Domiciliary care: (E) |
| Home Care: (N) | | Homecare: (E) |
| Prolonged Services | Factor | No 50% question |
| Physician Standby | Factor | No 50% question |
| Case Management | Factor | No 50% question |
| Care Plan Oversight Services | Factor | No 50% question |
| Preventive Medicine | | No 50% question |
| Counseling | Factor | No 50% question |
| Newborn Care | | No 50% question |
| Rest Home (N) | | Rest Home (E) |

">50% unit/floor-counseling coordination?" Service types: office/outpatient visit; office consultations

TABLE 1-continued

Service type Guidelines
Definitions: N = New patient, E = Established patient
upper area: History, Exam, Medical Decision key elements
50% question: amount of time spent in face-to-face contact with patient

| Must meet or exceed all of the key components of history, exam, medical decision-making (3/3) | Time | Must meet two of the three key components of history, exam, and medical decision-making (2/3) |
|---|---|---|

">50% unit/floor-counseling coordination?" Service types: nursing, assessment and subsequent, initial consult, inpatient hospital care, follow-up consultation
WHENEVER TIME IS AN ELEMENT OF DECISION-MAKING WE SHOULD ASK THE QUESTION OF
50% except for Critical Care, Preventive medicine, Prolonged services, Physician Standby, Case Management, Care Plan Oversight Services, and Counseling. Time then becomes the controlling factor, such that time can adust the CPT upward, should always compare which gives the greater code with key elements or key elements using time. Selection of the code is then based on which of the two gives the higher coding element.

FIG. 6 is an example of a decision table for determining a clinical status code for a particular type of service, i.e., Office (outpatient visits) Services. The decision table of FIG. 6 is shown in flow-chart chart form in FIG. 7.

5.5 Advantages of the Invention

The system and method of the invention permits physicians and other medical staff members to conveniently record patient-treatment data. The system and method may be used for developing historical data about physician workload in an inpatient or outpatient setting. Such historical data contributes to a better understanding of the professional resources actually used in a given practice during a particular period of time. That understanding in turn permits improved resource allocation, e.g., better scheduling of work for specific physicians (and other medical professionals) in a hospital or a group or solo practice to accommodate anticipated patient-care workload. Understanding the type of work most commonly done allows improved decisions on the type of professional manpower needed.

The inventive system and method permits a physician to record, accurately and precisely, patient care information in a manner that requires considerably less physician and staff time. As a result, more physician time can be spent actually rendering patient care. In addition, the quantity and quality of historical care information for a particular patient is enhanced, meaning that future care decisions for that patient can be based on a more complete medical history database. Moreover, such enhanced care information can be put to use in outcome studies to track the efficacy of specific treatment protocols. In many ways, including how specific diagnostic/treatment approaches can change the quantity and quality of medical professional man-hours.

It will also be understood by those of ordinary skill that the clinical status codes generated as described above are the same as those used in requesting payment from insurance companies. Considerable physician and staff time are saved, and precision and accuracy are significantly enhanced, by generating these clinical status codes automatically (at the point of service by the care-provider without any intermediary steps) from information recorded simultaneously with the provision of services.

It will be appreciated by those of ordinary skill having the benefit of this disclosure that numerous variations from the foregoing illustration will be possible without departing from the inventive concept described herein. Accordingly, it is the claims set forth below, and not merely the foregoing illustration, which are intended to define the exclusive rights claimed in this application program.

— — APPENDIX A

SERVICE TYPE GUIDELINES

Definitions:

N=New patient
E=Established patient upper area= History, Exam, Medical Decision key elements 50 % question = amount of time spent in contact with patient

| must meet or exceed all of the key components of history, exam, med-decision making (3/3) | TIME | must meet two of the three key components of history, exam, and med-decision making (2/3) |
|---|---|---|
| Office:(outpatient) (N) | factor | Office:(outpatient) (E) |
| Hosp observation services (N/E) | | |
| Initial hospital care (N/E) | factor | Subsequent Hospital Care |
| Office Consult (outpatient)(N/E) | factor | |
| Initial Inpatient Consult (N/E) | factor | Follow-up Inpatient Conslt.(E) |
| Confirmatory Consult (N/E) | | no 50% ques |
| Emergency Department | | |
| Critical care | factor | no 50% ques (based on 30min increments) |
| Neonatal Intensive care | | no 50% ques |
| Compr. Nursing facility (N/E) | factor | Subsequnt Nurs. facilty care (N/E) |

| Domiciliary care (rest home): (N) | | Domiciliary care :(E) |
|---|---|---|
| Home care: (N) | | Homecare: (E) |
| Prolonged services | factor | no 50% ques |
| Physician standby | factor | no 50% ques |
| Casemanagement | factor | no 50% ques |
| Care Plan Oversight Services | factor | no 50% ques |
| Preventive medicine | | no 50% ques |
| Counseling | factor | no 50% ques |
| Newborn care | | no 50% ques |
| Rest Home (N) | | Rest Home (E) |

">50% contact counseling/coordination?"
    for these service types:office/outpatient visit ; office consultaions
">50%unit/floor counseling/coordination?"
    for these service types: nursing: assessment & subsequent;initial
    consult;inpat. hospcare:follow-up consult WHEN EVER TIME IS AN ELEMENT OF DECISION MAKING WE SHOULD ASK THE QUESTION OF 50% except for *Crital Care ,Preventive medicine,Prolonged services, Physician Standby, Case Management, Care Plan Oversight Serivces, and Counseling* Time then becomes the controlling factor, *Such that time can adjust the CPT upward, Should always compare which gives the greater code with key elements or key elements using time. Selection of the code is then based on which of the two gives the higher coding element*

1- Office (outpatient visits) Services
    Ques? Any symptoms?
        no = Ques? Give physical?
            no = Ques? Provided Counseling?
                no = 99499
                yes = Prompt = go to couseling or risk reduction factor
    yes = using Preventive Medicine yes = use table below New (3/3)">50% contact counseling/coordination?"

| History | Exam | Medical Decis. | time | code |
|---|---|---|---|---|
| problem focused | problem focused | straight forward | <=19 | 99201 |
| expanded | expanded | straight forward | >=20 <=29 | 99202 |
| detailed | detailed | low complexity | >=30 <=44 | 99203 |
| comprehensive | comprehensive | moderate | >=45 <=59 | 99204 |
| comprehensive | comprehensive | high | >=60 | 99205 |

Estab (2/3)">50% contact counseling/coordination?"

| History | Exam | Medical Decis. | time | code |
|---|---|---|---|---|
| | | | | |
| focused | focused | straight forward | >=~~11~~ >=10<=14 | 99212 |
| expanded | expanded | low complexity | >=15 <=24 | 99213 |
| detailed | detailed | moderate | >=25 <=39 | 99214 |
| comprehensive | comprehensive | high | >=40 | 99215 |

2 - HOSPITAL INPATIENT SERVICES

Initial hospital care
                       (new or established)

Question? "Is this an admission?"
    yes - Intial Hospital Care
        Question? ">50%unit/floor counseling/coordination?"
           yes - use codes 99221 - 99223 with time as a factor
           no  - use codes 99221 - 99223 *no time as a factor*
    no - Subsequent Hospital Care
        Question? ">50%unit/floor counseling/coordination?"
           yes - use codes 99231 - 99233 (for Sub-Hospital Care) with time
           no  - use codes 99231 - 99233 (for Sub-Hospital Care) *no time*

(3/3)

| History | Exam | Medical Decis. | time | code |
|---|---|---|---|---|
| iF key elements do not combine with Med Dec. & time to meet the criteria of 3/3 then display "key elements not high enough" and go to default code | | | <=29 | 99499 |
| detailed/comprhsv | detailed/comprhs | straight frwd/low | >=30<=49 | 99221 |
| comprehensive | comprehensive | moderate | >=50 <=69 | 99222 |
| comprehensive | comprehensive | high | >=70 | 99223 |
| 3/24/94 added this expanded table for clarity | | | | |
| detailed/comprhsv | detailed/comprhs | straight frwd/low | <=49 | 99221 |
| 3 or 4 | 3 or 4 | 111,222,221 etc | | |
| comprehensive | comprehensive | moderate | >=50 <=69 | 99222 |
| 4 | 4 | 333,331,332,etc | | |
| comprehensive | comprehensive | high | >=70 | 99223 |
| 4 | 4 | 444,441,442,etc | | |
| | | | | |
| #2 Hosp Inpat should not look at New or Old because could be old/existing patient but a new admission                ask question "Is this an admission?"                if No and 50 % = yes (use codes 99221-99223 no time factor)                if Yes and 50% = no (use codes 99221-99223 with time as a factor) | | | | |

2. Subsequent hospital care
(established) (2/3) ">50%unit/floor counseling/coordination?"

| History | Exam | Medical Decis. | time | code |
|---|---|---|---|---|
| prob focused | problem focused | straight frwrd/low | <=24 | 99231 |
| expanded | expanded | moderate | >=25 <=34 | 99232 |
| detailed | detailed | high complexity | >=35 | 99233 |

CONSULTATIONS

-3-Office (Outpatient) Consultations
(new or established) (3/3) ">50% contact counseling/coordination?"

| History | Exam | Medical Decis. | code | time |
|---|---|---|---|---|
| prob focused | problem focused | straight forward | 99241 | <=29 |
| expanded | expanded | straight forward | 99242 | >=30 <=39 |
| deatiled | detailed | low complex | 99243 | >=40 <=59 |
| comprehensive | comprehensive | moderate | 99244 | >=60<=79 |
| comprehensive | comprehensive | high complexity | 99245 | >=80 |

-4-Consult-Initial Inpatient
(new/established) (3/3)">50%unit/floor counseling/coordination?"

| History | Exam | Medical Decis. | code | time |
|---|---|---|---|---|
| prob focused | problem focused | straight forward | 99251 | <=39 |
| expanded | expanded | straight forward | 99252 | >=40 <=54 |
| deatiled | detailed | low complex | 99253 | >=55 <=79 |
| comprehensive | comprehensive | moderate | 99254 | >=80<=109 |
| comprehensive | comprehensive | high complexity | 99255 | >=110 |

-5. Confirmatory consultation
(new or established) (3/3)
">50% unit/floor contact counseling/coordination?"

| History | Exam | Medical Decis. | code | time |
|---|---|---|---|---|
| focused | focused | straight forward | 99271 | none |
| expanded | expanded | straight forward | 99272 | none |
| detailed | detailed | low complexity | 99273 | none |
| comprehensive | comprehensive | moderate | 99274 | none |
| comprehensive | comprehensive | high | 99275 | none |
| #5 Conf Cons-no time necessary when answering YES.. | | | | |

-6-Emergency

Need to ask the question?
    Is this advanced life support?
        yes $\Rightarrow$ 99288
        no $\Rightarrow$ follow the table below

⇓

| History | Exam | Med Decision | CPT code |
|---|---|---|---|
| focused | focused | straight forward | 99281 |
| Expanded | Expanded | low complex | 99282 |
| Expanded | Expanded | Mod complex | 99283 |
| Detailed | Detailed | Mod complex | 99284 |
| Comprehensive | Comprehen | High. complx | 99285 |

-7- Critical Care Visit

1. Should select type of service then skip to the time field
2. If charge for 99291 has been entered that day for patient then always select the 99292 after the time is entered. Can Only bill for one hour at 99291. Add times together then bill at 30 min.

| Time | CPT code |
|---|---|
| <= 60 min | 99291 |
| > 60 min | 99292 |
| for every 30 min (thirty) after the first hour enter 99292 so if it is 2hrs beyond the first 60min then there would be 4(four) entries for 99292 | |

-8- NURSING SERVICES

Comprehensive Assessments

Question? "Subsequent Nursing facility
    no - Use Comprehensive Assessments
        Ques? "50%unit floor contact?"
            yes - use codes 99301 - 99303 with time factor
            no  - use codes 99301 99303 *no time factor*
    yes- Use Subsequent Care Facility
        Ques?"50%unit floor contact?"
            yes - use codes 99311 - 99313 with time factor
            no  - use codes 99311 -99313 *no time factor*

(new/established) (3/3)

| History | Exam | Medical Decis. | time | code | no time |
|---|---|---|---|---|---|
| detailed | comprehensive | straight frwrd/low | 39 <= | 99301 | 99301 |
| detailed | comprehensive | moderate/high | >=40 <=49 | 99302 | 99302 |
| comprehensive | comprehensive | high | >=50 | 99303 | 99303 |

2. Subsequent facility care (new/established) (2/3)

| History | Exam | Medical Decis. | time | code | no time |
|---|---|---|---|---|---|
| prob focused | problem focused | straight frwrd/low | <=24 | 99311 | 99311 |
| expanded | expanded | moderate | >=25<=34 | 99312 | 99312 |
| detailed | detailed | mod/high complexity | >=35 | 99313 | 99313 |

-9- Domciliary, Rest Home or Custodial Care (new) (3/3)

| History | Exam | Medical Decis. | time | code |
|---|---|---|---|---|
| prob focused | problem focused | straight frwrd/low | none | 99321 |
| expanded | expanded | moderate | none | 99322 |
| detailed | detailed | high complexity | none | 99333 |

(established) (2/3)

| History | Exam | Medical Decis. | time | code |
|---|---|---|---|---|
| prob focused | problem focused | straight frwrd/low | none | 99331 |
| expanded | expanded | moderate | none | 99332 |
| detailed | detailed | high complexity | none | 99333 |

-10- HOME SERVICES

1. Check to see if new or established
(once a person has a charge they are no longer "new". Upon entering a charge, the program should update the patient detail from "N" to "O")

(New) (3/3)

| History | Exam | Medical Decis. | time | code |
|---|---|---|---|---|
| prob focused | problem focused | straight frwrd/low | none | 99341 |
| expanded | expanded | moderate | none | 99342 |
| detailed | detailed | high complexity | none | 99343 |

(Established) (2/3)

| History | Exam | Medical Decis. | time | code |
|---|---|---|---|---|
| prob focused | problem focused | straight frwrd/low | none | 99351 |
| expanded | expanded | moderate | none | 99352 |
| detailed | detailed | high complexity | none | 99353 |

CASE MANAGEMENT SERVICES

-11-. Case Management Team

Should skip upper area and go directly to time

| time | code value |
|---|---|
| <= 60 min | 99361 |
| > than 61 | 99362 |

-12- Case Management Phone

1. Should skip upper area and go directly to CPT code field
2. Window should pop-up and allow selection
3. Upon selection the appropriate CPT code value would be return to the field POP-UP WINDOW          Value returned to field

| CALLS | CPT CODE VALUE |
|---|---|
| 1.SIMPLE/BRIEF | 99371 |
| 2. INTERMEDIATE | 99372 |
| 3. COMPLEX | 99373 |

-13- PREVENTIVE MEDICINE SERVICES
1. Should skip the upper area and go directly to CPT field
2. Need to check age- not sure if happening
3. Need to check patient detail to see if new or established patient
4. If no age or age is 01/01/0001 then need to prompt for age
    a. IF no age is entered abort entry with prompt
    b. IF age is entered, put in correct code and update the patient detail 1. New

| AGE | Code |
|---|---|
| >=1day <=364 days (one year) | 99381 |
| >=1 yr <=4yr 364 days | 99382 |
| >=5 yr <=11yr 364 days | 99383 |
| >=12yr <=17yr 364 days | 99384 |
| >=18yr <=39yr 364 days | 99385 |
| >=40yr <=64yr 364 days | 99386 |
| >=65 yrs | 99387 |

2. Estab

| AGE | Code |
|---|---|
| >=1day <=364 days (one year) | 99391 |
| >=1 yr <= 4yr 364 days | 99392 |
| >=5 yr <=11yr 364 days | 99393 |
| >=12yr <=17yr 364 days | 99394 |
| >=18yr <=39yr 364 days | 99395 |
| >=40yr <=64yr 364 days | 99396 |
| >=65 yrs | 99397 |

-14-Individual Counseling
1. Should skip upper area and go directly to time
2. Should prompt to enter time new/estab

| time | code value |
|---|---|
| <= 29 min | 99401 |
| > =30 <=44 min | 99402 |
| >=45 <=59 | 99403 |
| >= 60 min | 99404 |

-15- Group Counseling

1. Should skip upper area and go directly to time
2. Should prompt to enter time new/estab

| time | code value |
|---|---|
| <= 59 min | 99411 |
| >= than 60 | 99412 |

-17- Neonatal Intensive Care

1. Prompt with error message if more than one visit charge per day
2. Add type of service - Neonatal
3. Skip History, Exam, Medical Decision etc and go directly to CPT field with a pop-up POP-UP WINDOW      Value returned to field

| Service | CPT code |
|---|---|
| 1. Initial NICU | 99295 |
| 2. NICU Unstable | 99296 |
| 3. NICU Stable | 99297 |
| when user selects 1,2,or 3 the program puts the code into the CPT field ||

-18- Newborn

When selection of visit for this service type is made should SKIP top portion and go directly to CPT field where window pops up

| Service | CPT code |
|---|---|
| 1. History, exam, diag | 99431 |
| 2. Other than hospital care | 99432 |
| 3. Sub hosp care | 99433 |
| 4. Resuscitation/ High Risk | 99440 |
| when user selects 1,2,3, or 4 the program puts the code into the CPT field ||

-19 Consults inpatient follow-up

Estab(2/3) ">50% unit/floor contact counseling/coordination?"

| History | Exam | Medical Decis. | code | time |
|---|---|---|---|---|
| prob focused | problem focused | straight forward | 99261 | <=20min |
| expanded | expanded | moderat complx | 99262 | >20min<=29min |
| detailed | detailed | highly complx | 99263 | =>30min |

-20-Hospital Discharge
Don't enter anything but code = 99238

-21- HOSPITAL OBSERVATION
">50% unit/floor contact counseling/coordination?"

| History | Exam | Medical Decis. | CPT Code |
|---|---|---|---|
| Detailed/Comp | Detailed/Comp | Strgth Frwd/Low | 99218 |
| Comprehensive | Comprehensive | Moderate Cmplx | 99219 |
| Comprehensive | Comprehensive | Highly Complex | 99220 | should not need both, just ask question "Is this the discharge day from observation? if yes then give code 99217 if NO then give code 99218 to 99220 or dump to 99499 if key elements are lower than in table

16 Observation
should not need both 16 & 21, just ask question "Is this the discharge day from observation?
    if YES then give code 99217
    if NO then give code 99218 to 99220
    if key elements are lower than in table
dump to 99499

-22-PROLONGED SERVICES
ask the question:
 Is this Stanby Service? Y/N
 If YES
 a. Physician Standby Service
  <= 29 abort charge message "not enough time"
  >=30 <=60 = 99360 then report same code at multiples of exactly 30 min
 If NO
  Needs to ask the question:
   Face to Face? Y/N
    b. If YES (Prolonged Service with Face to Face Contact)
     Needs to ask the question:
     Is this an inpatient?
      If YES
       1. <30 min abort charge with message saying "not enough time"
       2. >31<74 = 99356
       3. >=75 = 99356 + 99357 for multiples of each additional 30 min
      If NO
       1. <30 min abort charge with message saying "cannot report time seperately"
       2. >31<74 = 99534
       3. >=75 = 99534 + 99355 for multiples of each additional 30 min c. If NO(<u>Prolonged Service without direct Face to Face contact</u>)
   (can be used only once per date, but time does not have to be continuous)
   1. <=29 abort with message "not enough time)
   2. >=30 <=74 = 99358
   3. >=75 = 99358 + multiples of 99359 for every 30 min (except if last is less than 15 min)

---

3/8/94 #21Prolonged
    Stanby service = Y
    50% Face to Face = N then N,N
    60 min not = 99358 + see CPT chart
Ques? of 50% "Face to Face contact?"

---

Total Duration of Prolonged Services
Office or Outpatient - With Face to Face

| TIME | PROMPT | Code | BASE STATION RESULT |
|---|---|---|---|
| <= 29 | "not enough time" | none | Nothing |
| >=30 <=74 | none | 99354 | 99354 |
| >=75 <=104 | none | 99354+ | 99354(1) & 99355(1) |
| >=105<=134 | none | 99354+ | 99354(1) & 99355(2) |
| >=135<=164 | none | 99354+ | 99354(1) & 99355(3) |
| >=165<=194 | none | 99354+ | 99354(1) & 99355(4) |

Total Duration of Prolonged Services
Inpatient- With Face to Face

| TIME | PROMPT | Code | BASE STATION RESULT |
|---|---|---|---|
| <= 29 | "not enough time" | none | Nothing |
| >=30 <=74 | none | 99356 | 99356 |
| >=75 <=104 | none | 99356+ | 99356(1) & 99357(1) |
| >=105<=134 | none | 99356+ | 99356(1) & 99357(2) |
| >=135<=164 | none | 99356+ | 99356(1) & 99357(3) |
| >=165<=194 | none | 99356+ | 99356(1) & 99357(4) |

Total Duration of Prolonged Services
Without Face to Face

| TIME | PROMPT | Code | BASE STATION RESULT |
|---|---|---|---|
| <= 29 | "not enough time" | none | Nothing |
| >=30 <=74 | none | 99358 | 99358 |
| >=75 <=104 | none | 99358+ | 99358(1) & 99359(1) |
| >=105<=134 | none | 99358+ | 99358(1) & 99359(2) |
| >=135<=164 | none | 99358+ | 99358(1) & 99359(3) |
| >=165<=194 | none | 99358+ | 99358(1) & 99359(4) |

21Prolonged eliminate based on question of #16 HOWEVER if you answer in #16
Stanby service = Y
50% Face to Face = N then N,N
60 min not = 99358 + see CPT chart
Ques? of 50% Face to Face should read only "Face to Face contact?"

Physician standby service
Ques? Are you caring for other patients?
Yes =Prompt "select another service type"
No = >= 30 min 99360
99360+ = 30 min exactly------

| TIME | PROMPT | Code | BASE STATION RESULT |
|---|---|---|---|
| <= 29 | "not enough time" | none | Nothing |
| >=30 <=59 | none | 99360 | 99360 |
| >=30 <=89 | none | 99360+ | 99360 (2) |
| >=30 <=119 | none | 99360+ | 99360 (3) |
| >=30<=120 | none | 99360+ | 99360 (4) |
| etc | etc | etc | billed only in 30 min increments |

??.CARE PLAN OVERSIGHT SERVICES
Go directly to time.
If no time prompt "must enter time
no time = abort charge (after user tries twice not to enter time?)
yes time <= 29 min =prompt "Not enough time,
"not a billable service"(take to service type field)
time >= 30 min =Ques? "Are you the predominent physician?
no = prompt "use another service type"
yes= check date >=1<=30 days (from initial reporting of this service type)
no = prompt "beyond 30 days" ---HERE---
yes = ⇩

| TIME | PROMPT | Code |
|---|---|---|
| <= 29 | "not enough time, use another service type" | none |
| >=30 <=60 | none | 99375 |
| >=61 | none | 99376 |

What needs to happen here is the time should be added up for the 29days if it meets the time criteria the base would report it at the end of 29days as a billable service, if not then it would not be billable. Then the cycle begins again for the next 30days.

What is claimed is:

1. A method, executed by a system including a device operated by a medical staff member, of generating a signal encoding a clinical status code that quantifies a physician intervention status of a patient as an objective measure of a physician's rendered level of care of the patient and of using the signal in generating a billing document containing said clinical status code, said clinical status code being determinable as a function of (I) a level of medical history of said patient, a level of physical examination of said patient, and a medical decision-making process of said physician treating said patient, referred to as key elements of said clinical status code, (ii) a time influence factor determined as a function of a service time defined as one or more of (1) an amount of unit floor time or face-to-face time spent by said physician in connection with an encounter with said patient, or (2) an amount of time spent by said physician in counseling or coordination of care for said patient, said method comprising:
(a) prompting the staff member to select a service type, referred to as a selected service type;
(b) displaying to said staff member a series of questions, said series of questions being determined by said selected service type;
(c) if said selected service type is associated with a time influence factor, then prompting the staff member to enter an amount of service time;
(d) if the selected service type does not fall within an exception category, then determining said clinical status code as a function of (I) said selected service type, (ii) said levels and said medical decision-making process, and (iii) if the staff member entered an amount of service time, said amount of service time; and
(e) generating a signal encoding said determined clinical status code and using said signal in generating a billing document containing said clinical status code.

2. The method of claim 1, further comprising:
(f) prompting the staff member to select at least one of a plurality of diagnoses that are applicable to said patient, each referred to as a selected diagnosis, and
(g) determining a diagnosic code corresponding to said selected diagnosis and generating a signal encoding said diagnosis code.

3. The method of claim 1, wherein said selected service type is selected from the group consisting of (i) outpatient services, (ii) hospital observation services, (iii) hospital in-patient services, (iv) hospital discharge services, (v) outpatient consultations, (vi) in-patient consultations, (vii) in-patient follow-up consultations, (viii) confirmatory consultations, (ix) emergency services, (x) critical care visits, (xi) neonatal intensive care, (xii) nursing facility services, (xiii) domiciliary, rest home, or custodial care, (xiv) home services, (xv) prolonged services, (xvi) case management team services, (xvii) case management phone services, (xviii) care plan oversight services, (xix) preventive medicine services, (xx) preventive medicine individual counseling, (xxi) preventive medicine group counseling, and (xxii) newborn care.

4. The method of claim 1, wherein said exception category is selected from a group consisting of hospital discharge services, observation discharge services, critical care, care plan oversight services, case management team services, prolonged services, neonatal intensive care, case management phone services, preventive medicine services, emergency advanced life support services, and newborn care.

5. The method of claim 4, wherein (1) said selected service type is neonatal intensive care and (2) said clinical status code is further determinable as a function of (i) a neonatal patient stability factor, and (ii) whether the service constituted initial care or subsequent care.

6. The method of claim 4, wherein (1) said selected service type is case management phone services, and (2) said clinical status code is further determinable as a function of a complexity-of-call factor.

7. The method of claim 4, wherein (1) said selected service type is preventive medicine services, and (2) said clinical status code is further determinable as a function of the age of the patient.

8. The method of claim 4, wherein (1) said selected service type is newborn care, and (2) said clinical status code is further determinable as a function of (i) whether the newborn care is given at a hospital or at a location other than a hospital, (ii) whether one or more specified risk factors is present, and (iii) whether the service constituted initial care or subsequent care.

9. The method of claim 4, wherein (1) said selected service type is hospital discharge services, and (2) said clinical status code is further determinable solely as a function of said selected service type.

10. The method of claim 4, wherein (1) said selected service type is hospital observation discharge services, and (2) said clinical status code is further determinable solely as a function of said selected service type.

11. The method of claim 4, wherein (1) said selected service type is critical care, and (2) said clinical status code is further determinable as a function of the amount of service time.

12. The method of claim 4, wherein (1) said selected service type is care plan oversight services, and (2) said clinical status code is further determinable as a function of the amount of service of time provided during any consecutive 30 day period.

13. The method of claim 4, wherein (1) said selected service type is case management team services, and (2) said clinical status code is further determinable as a function of (i) selected service type, and (ii) amount of time the physician spends in conference with another health care professional to coordinate activities for patient care.

14. The method of claim 4, wherein (1) said selected service type is prolonged services, and (2) said clinical status code is further determinable as a function of (i) whether said prolonged services are provided in an in-patient setting or an out-patient basis, (ii) whether said prolonged services are provided with or without said patient being present and (iii) the amount of service time.

15. The method of claim 4, wherein (1) said selected service type is emergency advanced life support services, and (2) said clinical status code is further determinable solely as a function of said selected service type.

16. The method of claim 1, wherein said plurality of allowable levels for each key element consists of four allowable levels for each key element.

17. The method of claim 1, further comprising determining whether the respective selected levels meet a specified set of key-component criteria and if not, assigning a default code as said clinical status code.

18. In a physician's practice management system, a device operable by a medical staff member for recording a clinical status code that quantifies a physician intervention status of a patient as an objective measure of a physician's rendered level of care of the patient, said clinical status code being determinable as a function of (I) a level of medical history of said patient, a level of physical examination of said patient, and a medical decision-making process of a physician treating said patient, referred to as key elements of said clinical status code, (ii) a time influence factor determined as a function of a service time defined as one or more of (1) an amount of unit floor time or face-to-face time spent by said physician in connection with an encounter with said patient, or (2) an amount of time spent by said physician in counseling or coordination of care for said patient, said device comprising:
- (a) means for prompting the physician to select a service type, referred to as a selected service type;
- (b) means for prompting the physician to select, for each respective key element of said clinical status code, one of a plurality of allowable levels for said respective key element, referred to as a selected level;
- (c) means for prompting the physician to enter an amount of service time if said selected service type is associated with a time influence factor;
- (d) means for determining said clinical status code as a function of (I) said selected service type, (ii) said levels and said medical decision-making process, and (iii) if the physician entered an amount of service time, said amount of service time; and
- (e) means for transmitting the determined clinical status code to a computer that includes means for generating a payment request.

* * * * *